United States Patent
Bar-El et al.

(10) Patent No.: US 10,251,813 B2
(45) Date of Patent: Apr. 9, 2019

(54) FLEXIBLY MOUNTED CARTRIDGE ALIGNMENT COLLAR FOR DRUG DELIVERY DEVICE

(71) Applicant: MEDIMOP Medical Projects Ltd., Ra'anana (IL)

(72) Inventors: Yossi Bar-El, Beit Arye (IL); Tomer Solomon, Modiin (IL); Reuven Y. Filman, Netanya (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 900 days.

(21) Appl. No.: 14/638,713

(22) Filed: Mar. 4, 2015

(65) Prior Publication Data
US 2016/0256353 A1    Sep. 8, 2016

(51) Int. Cl.
*A61M 5/32*      (2006.01)
*A61J 1/14*       (2006.01)
(Continued)

(52) U.S. Cl.
CPC .......... *A61J 1/1406* (2013.01); *A61M 5/1413* (2013.01); *A61M 5/1456* (2013.01);
(Continued)

(58) Field of Classification Search
CPC .. A61J 1/1406; A61M 5/1413; A61M 5/1456; A61M 5/1782; A61M 5/24; A61M 5/34; A61M 5/158
See application file for complete search history.

(56) References Cited

U.S. PATENT DOCUMENTS 3,994,295 A    11/1976   Wulff
4,601,702 A     7/1986   Hudson
(Continued)

FOREIGN PATENT DOCUMENTS

EP    0401179 A1    12/1990
EP    1249250 A1    10/2002
(Continued)

OTHER PUBLICATIONS

Extended Search Report dated Jun. 13, 2016 in EP Application No. 16157430.6.
(Continued)

*Primary Examiner* — Ariana Zimbouski
(74) *Attorney, Agent, or Firm* — Panitch Schwarze Belisario & Nadel LLP

(57) ABSTRACT

An alignment assembly for a cartridge interface of a drug delivery device is disclosed. The assembly optionally includes a coupling for opening fluid communication between the cartridge and the delivery device. For example, the coupling optionally includes a cannula insertable through a septum of the cartridge. The assembly may include a guide for positioning the cartridge and/or an access channel thereof within a first precision of a loaded position. The assembly optionally includes a cartridge engagement fitting (for example a gripping expander sleeve collar) attached to the coupling. Optionally when the cartridge is engaged to the fitting, the coupling is retained in connection with the access channel to within a second precision. The second precision is optionally higher than the first precision. In some embodiments one or more compliant supports movably retain the fitting oriented to engage the cartridge when the access channel is in the loaded position.

15 Claims, 11 Drawing Sheets

(51) Int. Cl.
  *A61M 5/178* (2006.01)
  *A61M 5/145* (2006.01)
  *A61M 5/14* (2006.01)
  *A61M 5/24* (2006.01)
  *A61M 5/34* (2006.01)

(52) U.S. Cl.
  CPC ............ *A61M 5/1782* (2013.01); *A61M 5/24* (2013.01); *A61M 5/34* (2013.01); *A61M 2209/045* (2013.01)

(56) References Cited

U.S. PATENT DOCUMENTS

| | | |
|---|---|---|
| 4,886,499 A | 12/1989 | Cirelli et al. |
| 4,919,596 A | 4/1990 | Slate et al. |
| 4,950,246 A | 8/1990 | Muller |
| 5,097,122 A | 3/1992 | Colman et al. |
| 5,109,850 A | 5/1992 | Blanco et al. |
| 5,131,816 A | 7/1992 | Brown et al. |
| 5,211,638 A | 5/1993 | Dudar et al. |
| 5,254,096 A | 10/1993 | Rondelet et al. |
| 5,383,865 A | 1/1995 | Michel |
| 5,501,665 A | 3/1996 | Jhuboo et al. |
| 5,593,390 A | 1/1997 | Castellano et al. |
| 5,616,132 A | 4/1997 | Newman |
| 5,643,218 A | 7/1997 | Lynn et al. |
| 5,647,853 A | 7/1997 | Feldmann et al. |
| 5,690,618 A | 11/1997 | Smith et al. |
| D393,314 S | 4/1998 | Meisner et al. |
| 5,800,420 A | 9/1998 | Gross et al. |
| 5,807,375 A | 9/1998 | Gross et al. |
| 5,814,020 A | 9/1998 | Gross |
| 5,851,197 A | 12/1998 | Marano et al. |
| 5,858,001 A | 1/1999 | Tsals et al. |
| 5,858,008 A | 1/1999 | Capaccio |
| 5,931,814 A | 8/1999 | Alex et al. |
| 5,957,895 A | 9/1999 | Sage et al. |
| 5,993,423 A | 11/1999 | Choi |
| 6,004,297 A | 12/1999 | Steenfeldt-Jensen et al. |
| 6,064,797 A | 5/2000 | Crittendon et al. |
| 6,074,369 A | 6/2000 | Sage et al. |
| 6,186,982 B1 | 2/2001 | Gross et al. |
| 6,200,289 B1 | 3/2001 | Hochman et al. |
| 6,248,093 B1 | 6/2001 | Moberg |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,362,591 B1 | 3/2002 | Moberg |
| 6,391,005 B1 | 5/2002 | Lum et al. |
| 6,423,029 B1 | 7/2002 | Elsberry |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,517,517 B1 | 2/2003 | Farrugia et al. |
| D471,274 S | 3/2003 | Diaz et al. |
| D471,983 S | 3/2003 | Hippolyte et al. |
| 6,555,986 B2 | 4/2003 | Moberg |
| 6,558,351 B1 | 5/2003 | Steil et al. |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,699,218 B2 | 3/2004 | Flaherty et al. |
| 6,749,587 B2 | 6/2004 | Flaherty |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,817,990 B2 | 11/2004 | Yap et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |
| 6,960,192 B1 | 11/2005 | Flaherty et al. |
| 7,001,360 B2 | 2/2006 | Veasey et al. |
| 7,048,715 B2 | 5/2006 | Diaz et al. |
| 7,060,059 B2 | 6/2006 | Keith et al. |
| 7,128,727 B2 | 10/2006 | Flaherty et al. |
| 7,144,384 B2 | 12/2006 | Gorman et al. |
| 7,193,521 B2 | 3/2007 | Moberg et al. |
| D544,092 S | 6/2007 | Lewis |
| 7,247,149 B2 | 7/2007 | Beyerlein |
| 7,247,150 B2 | 7/2007 | Bierman |
| 7,250,037 B2 | 7/2007 | Shermer et al. |
| 7,267,669 B2 | 9/2007 | Staunton et al. |
| 7,303,549 B2 | 12/2007 | Flaherty et al. |
| 7,384,413 B2 | 6/2008 | Gross et al. |
| 7,390,314 B2 | 6/2008 | Stutz, Jr. et al. |
| 7,407,493 B2 | 8/2008 | Cane' |
| 7,455,663 B2 | 11/2008 | Bikovsky |
| 7,465,290 B2 | 12/2008 | Reilly |
| 7,497,842 B2 | 3/2009 | Diaz et al. |
| 7,530,964 B2 | 5/2009 | Lavi et al. |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| D602,155 S | 10/2009 | Foley et al. |
| D602,586 S | 10/2009 | Foley et al. |
| D604,835 S | 11/2009 | Conley |
| 7,621,893 B2 | 11/2009 | Moberg et al. |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,227 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,903 B2 | 5/2010 | Estes et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,766,873 B2 | 8/2010 | Moberg et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,801,599 B2 | 9/2010 | Young et al. |
| 7,806,868 B2 | 10/2010 | De Polo et al. |
| 7,815,622 B2 | 10/2010 | Istoc et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,857,131 B2 | 12/2010 | Vedrine |
| 7,879,025 B2 | 2/2011 | Jacobson et al. |
| 7,879,026 B2 | 2/2011 | Estes et al. |
| 7,892,206 B2 | 2/2011 | Moberg et al. |
| 7,918,825 B2 | 4/2011 | O'Connor et al. |
| 7,918,843 B2 | 4/2011 | Genosar et al. |
| 7,935,104 B2 | 5/2011 | Yodfat et al. |
| 7,935,105 B2 | 5/2011 | Miller et al. |
| 7,938,803 B2 | 5/2011 | Mernoe et al. |

(56) References Cited

U.S. PATENT DOCUMENTS

| | | |
|---|---|---|
| 7,955,297 B2 | 6/2011 | Radmer et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,981,105 B2 | 7/2011 | Adair et al. |
| 7,988,683 B2 | 8/2011 | Adair et al. |
| 7,993,300 B2 | 8/2011 | Nyholm et al. |
| 7,998,111 B2 | 8/2011 | Moberg et al. |
| 7,998,116 B2 | 8/2011 | Mernoe |
| 7,998,117 B2 | 8/2011 | Gross et al. |
| 8,002,752 B2 | 8/2011 | Yodfat et al. |
| 8,021,357 B2 | 9/2011 | Tanaka et al. |
| 8,025,658 B2 | 9/2011 | Chong et al. |
| 8,029,459 B2 | 10/2011 | Rush et al. |
| 8,029,460 B2 | 10/2011 | Rush et al. |
| 8,029,469 B2 | 10/2011 | Ethelfeld |
| 8,034,019 B2 | 10/2011 | Nair et al. |
| 8,038,648 B2 | 10/2011 | Marksteiner |
| 8,038,666 B2 | 10/2011 | Triplett et al. |
| 8,057,436 B2 | 11/2011 | Causey et al. |
| 8,062,253 B2 | 11/2011 | Nielsen et al. |
| 8,062,257 B2 | 11/2011 | Moberg et al. |
| 8,062,259 B2 | 11/2011 | Nycz et al. |
| 8,065,096 B2 | 11/2011 | Moberg et al. |
| 8,066,694 B2 | 11/2011 | Wagener |
| D650,079 S | 12/2011 | Presta et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,157,769 B2 | 4/2012 | Cabiri |
| 8,162,923 B2 | 4/2012 | Adams et al. |
| 8,167,841 B2 | 5/2012 | Teisen-Simony et al. |
| 8,172,804 B2 | 5/2012 | Bikovsky |
| 8,182,447 B2 | 5/2012 | Moberg et al. |
| 8,182,462 B2 | 5/2012 | Istoc et al. |
| 8,197,444 B1 | 6/2012 | Bazargan et al. |
| 8,206,296 B2 | 6/2012 | Jennewine |
| 8,206,351 B2 | 6/2012 | Sugimoto et al. |
| 8,221,356 B2 | 7/2012 | Enggaard et al. |
| 8,221,359 B2 | 7/2012 | Kristensen et al. |
| 8,226,607 B2 | 7/2012 | Carter et al. |
| 8,226,608 B2 | 7/2012 | Mernoe |
| 8,234,769 B2 | 8/2012 | Leidig |
| 8,267,893 B2 | 9/2012 | Moberg et al. |
| 8,267,921 B2 | 9/2012 | Yodfat et al. |
| 8,287,520 B2 | 10/2012 | Drew et al. |
| 8,308,679 B2 | 11/2012 | Hanson et al. |
| 8,361,028 B2 | 1/2013 | Gross et al. |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,483,980 B2 | 7/2013 | Moberg et al. |
| 8,495,918 B2 | 7/2013 | Bazargan et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,574,216 B2 | 11/2013 | Istoc et al. |
| 8,603,026 B2 | 12/2013 | Favreau |
| 8,603,027 B2 | 12/2013 | Favreau |
| 8,617,110 B2 | 12/2013 | Moberg et al. |
| 8,628,510 B2 | 1/2014 | Bazargan et al. |
| 8,647,074 B2 | 2/2014 | Moberg et al. |
| 8,647,296 B2 | 2/2014 | Moberg et al. |
| 8,668,672 B2 | 3/2014 | Moberg et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| 8,690,855 B2 | 4/2014 | Alderete, Jr. et al. |
| 8,708,961 B2 | 4/2014 | Field et al. |
| 8,715,237 B2 | 5/2014 | Moberg et al. |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,808,269 B2 | 8/2014 | Bazargan et al. |
| 8,810,394 B2 | 8/2014 | Kalpin |
| 8,864,739 B2 | 10/2014 | Moberg et al. |
| 8,870,818 B2 | 10/2014 | Alderete, Jr. et al. |
| 8,992,475 B2 | 3/2015 | Mann et al. |
| 9,011,371 B2 | 4/2015 | Moberg et al. |
| 9,033,924 B2 | 5/2015 | Yavorsky |
| 9,050,406 B2 | 6/2015 | Kow et al. |
| 2001/0034502 A1 | 10/2001 | Moberg et al. |
| 2002/0040208 A1 | 4/2002 | Flaherty et al. |
| 2002/0055711 A1 | 5/2002 | Lavi et al. |
| 2003/0078195 A1* | 4/2003 | Kristensen ............ A61M 5/24 604/201 |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2004/0010207 A1 | 1/2004 | Flaherty et al. |
| 2004/0085215 A1 | 5/2004 | Moberg et al. |
| 2004/0260233 A1 | 12/2004 | Garibotto et al. |
| 2005/0065472 A1 | 3/2005 | Cindrich et al. |
| 2005/0071487 A1 | 3/2005 | Lu et al. |
| 2005/0171487 A1 | 8/2005 | Haury et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0238507 A1 | 10/2005 | Dilanni et al. |
| 2006/0095014 A1 | 5/2006 | Ethelfeld |
| 2006/0122577 A1 | 6/2006 | Poulsen et al. |
| 2006/0173439 A1 | 8/2006 | Thorne et al. |
| 2006/0184154 A1 | 8/2006 | Moberg et al. |
| 2006/0229569 A1 | 10/2006 | Lavi et al. |
| 2006/0264890 A1 | 11/2006 | Moberg et al. |
| 2006/0283465 A1 | 12/2006 | Nickel et al. |
| 2007/0021733 A1 | 1/2007 | Hansen et al. |
| 2007/0049865 A1 | 3/2007 | Radmer et al. |
| 2007/0118405 A1 | 5/2007 | Campbell et al. |
| 2007/0149926 A1 | 6/2007 | Moberg et al. |
| 2007/0191770 A1 | 8/2007 | Moberg et al. |
| 2007/0282269 A1 | 12/2007 | Carter et al. |
| 2008/0033369 A1 | 2/2008 | Kohlbrenner et al. |
| 2008/0051711 A1 | 2/2008 | Mounce et al. |
| 2008/0059133 A1 | 3/2008 | Edwards et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0215006 A1 | 9/2008 | Thorkild |
| 2008/0221522 A1 | 9/2008 | Moberg et al. |
| 2008/0221523 A1 | 9/2008 | Moberg et al. |
| 2008/0269723 A1 | 10/2008 | Mastrototaro et al. |
| 2008/0275425 A1 | 11/2008 | Strickler et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |

(56) References Cited

U.S. PATENT DOCUMENTS

| | | |
|---|---|---|
| 2009/0054750 A1 | 2/2009 | Jennewine |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1* | 4/2009 | Gross ............... A61M 5/14248 604/518 |
| 2009/0124977 A1 | 5/2009 | Jensen |
| 2009/0149830 A1 | 6/2009 | Spector |
| 2009/0182277 A1 | 7/2009 | Carter |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0299397 A1 | 12/2009 | Ruan et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0037680 A1 | 2/2010 | Moberg et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0145303 A1 | 6/2010 | Yodfat et al. |
| 2010/0162548 A1 | 7/2010 | Leidig |
| 2010/0168607 A1 | 7/2010 | Miesel |
| 2010/0198157 A1 | 8/2010 | Gyrn et al. |
| 2010/0204657 A1 | 8/2010 | Yodfat et al. |
| 2010/0212407 A1 | 8/2010 | Stringham et al. |
| 2010/0217192 A1 | 8/2010 | Moberg et al. |
| 2010/0217193 A1 | 8/2010 | Moberg et al. |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0119033 A1 | 5/2011 | Moberg et al. |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0178472 A1 | 7/2011 | Cabiri |
| 2011/0201998 A1 | 8/2011 | Pongpairochana et al. |
| 2011/0224614 A1 | 9/2011 | Moberg et al. |
| 2011/0238031 A1 | 9/2011 | Adair et al. |
| 2011/0245773 A1 | 10/2011 | Estes et al. |
| 2011/0264383 A1 | 10/2011 | Moberg et al. |
| 2011/0270160 A1 | 11/2011 | Mernoe |
| 2011/0282282 A1 | 11/2011 | Lorenzen et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022499 A1 | 1/2012 | Anderson et al. |
| 2012/0025995 A1 | 2/2012 | Moberg et al. |
| 2012/0029431 A1 | 2/2012 | Hwang et al. |
| 2012/0035546 A1* | 2/2012 | Cabiri ............... A61M 5/14248 604/151 |
| 2012/0041364 A1 | 2/2012 | Smith |
| 2012/0041370 A1 | 2/2012 | Moberg et al. |
| 2012/0041414 A1 | 2/2012 | Estes et al. |
| 2012/0071828 A1 | 3/2012 | Tojo et al. |
| 2012/0078217 A1 | 3/2012 | Smith et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0215169 A1 | 8/2012 | Moberg et al. |
| 2012/0215199 A1 | 8/2012 | Moberg et al. |
| 2012/0226234 A1 | 9/2012 | Bazargan et al. |
| 2012/0259282 A1 | 10/2012 | Alderete, Jr. et al. |
| 2012/0310153 A1 | 12/2012 | Moberg et al. |
| 2013/0012873 A1 | 1/2013 | Gross et al. |
| 2013/0068319 A1 | 3/2013 | Plumptre et al. |
| 2013/0096509 A1 | 4/2013 | Avery et al. |
| 2013/0133438 A1 | 5/2013 | Kow et al. |
| 2013/0148270 A1 | 6/2013 | Fujioka et al. |
| 2013/0237953 A1 | 9/2013 | Kow et al. |
| 2013/0245595 A1 | 9/2013 | Kow et al. |
| 2013/0253419 A1 | 9/2013 | Favreau |
| 2013/0253420 A1 | 9/2013 | Favreau |
| 2013/0253421 A1 | 9/2013 | Favreau |
| 2013/0253472 A1 | 9/2013 | Cabiri |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0194819 A1 | 7/2014 | Maule et al. |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |

FOREIGN PATENT DOCUMENTS

| | | |
|---|---|---|
| EP | 2412395 A1 | 2/2012 |
| EP | 2712650 A1 | 4/2014 |
| WO | 9009202 A1 | 8/1990 |
| WO | 9632975 A1 | 10/1996 |
| WO | 2011090955 A1 | 7/2011 |
| WO | 2011141907 A1 | 11/2011 |

OTHER PUBLICATIONS

Chan et al.; "Manufacturing Consideration in Developing a Prefilled Syringe Investigating the Effect of Headspace Pressure"; American Pharmaceutical Review, downloaded from webpage <https://www.americanpharmaceuticalreview.com/Featured-Articles/112325-Manufacturing-Consideration-in-Developing-a-Prefilled-Syringe-Investigating-the-Effect-of-Headspace-Pressure/>, May 8, 2012, 7 pages.

Edwards et al., "Appendix 3 Measurement of Leakage of Tuberculin Syringes"; World Health Organization Monograph Series No. 12; BCG Vaccination, Tuberculosis Research Office World Health Organization Copenhagen; World Health Organization; Palais Des Nations, Geneva, 1953.

\* cited by examiner

FLEXIBLY MOUNTED CARTRIDGE ALIGNMENT COLLAR FOR DRUG DELIVERY DEVICE

CROSS REFERENCE TO RELATED APPLICATION

This application is related to U.S. Patent Application titled "COMPLIANT COUPLING ASSEMBLY FOR CARTRIDGE COUPLING OF A DRUG DELIVERY DEVICE" to the same Applicant and filed on the same day, which is hereby incorporated by reference in its entirety.

BACKGROUND OF THE INVENTION

The present invention, in some embodiments thereof, relates to a coupling alignment system for a drug cartridge and, more particularly, but not exclusively, to a collar for aligning a cannula with a septum of a drug cartridge.

U.S. Patent Application Publication No. 2014/0083517 discloses "an alignment device for coupling a liquid drug cartridge with a longitudinal cartridge axis and a constricted neck portion with a cap and a piercable septum distal from the neck portion with an adapter . . . " "The septum is perpendicular to the cartridge axis. The device comprises an adapter cannula with a longitudinal cannula axis to pierce the septum and a proximal cartridge engagement structure for axial aligned engagement with a distal end section of cartridge body. The device further comprises a distal adapter engagement structure for axial aligned engagement with the adapter. A coupling of the cartridge with the adapter is enabled via the alignment device. The adapter and the cartridge are, during the coupling, aligned by the cartridge engagement structure and the adapter engagement structure, respectively relative to each other such that the longitudinal cartridge axis and the longitudinal cannula axis form a common longitudinal axis."

U.S. Patent Application Publication No. 2012/0029431 discloses "A reservoir and straight-line, push-on connector assembly" . . . "for connecting the reservoir and one of a standard Luer line set and a custom Luer line set to any number of infusion pump configurations using a simple straight-line, push-on motion, wherein the push-on connector assembly is provided and configured to secure the line set and reservoir with the infusion pump. One simple straight-line, push-on motion, preferably performed by gripping an expander sleeve, places and secures the reservoir (i.e., locates the reservoir on the x, y, and z axes) in the pump reservoir cavity, and one simple straight-line, pull-off motion releases and removes the reservoir from the pump reservoir cavity. Rotational orientation is not required for connection, pump engagement, or pump function, and any pulling of the tube set will not release the reservoir as the expansion sleeve through which the tube set is routed is not moved from the securing position by tension on the tube set or Luer fitting."

U.S. Patent Application Publication No. 2013/0096509 discloses "A system for a drug delivery device comprising a reservoir holder configured to hold a reservoir, and an alignment interface comprising a main body configured to be coupled to the reservoir. A first alignment feature is provided on the main body. The first alignment feature cooperates with a corresponding alignment feature provided by the reservoir holder such that when the reservoir is inserted into the holder, the first alignment feature cooperates with the corresponding alignment feature provided by the holder so as to rotate the alignment interface and thereby align the alignment interface within the holder. Thus, the reservoir may be aligned within the reservoir holder. The first alignment feature may comprise at least one protrusion provided on the main body of the interface. The system further comprises one or more coding features."

U.S. Patent Application Publication No. 2011/0054400 discloses that, "a piercing member for piercing a membrane may be arranged within a housing and supported by a compliant that may be for allowing articulation of the piercing member relative to the housing in a case where the piercing member is in the membrane and moved relative to the housing."

U.S. Patent Application Publication No. 2013/0148270 discloses a method and apparatus, "for delivery of a drug to a recipient. In some embodiments, the delivery apparatus may unseal a drug containing reservoir. In some embodiments, the delivery rate may be controlled and/or adjustable. Optionally the apparatus may be disposable. Optionally, the apparatus may have a low profile and/or be wearable and/or attachable to the recipient. Optionally, discharge of the drug and/or unsealing of the reservoir may be driven by a plunger moving parallel to the base of the apparatus. Optionally, the apparatus may release a hypodermic needle into the recipient. Optionally, release of the hypodermic needle may be in a direction non-parallel and/or orthogonal to the direction of movement of the plunger. Optionally, prior to release, the hypodermic needle may be preserved in an aseptic state by a needle opening septum sealing a needle opening. Optionally, upon release, the hypodermic needle may pierce the needle opening septum."

U.S. Pat. No. 6,595,960 discloses, "an apparatus and method of providing a flexible needle assembly for use with a medication delivery pen. The flexible needle assembly includes a needle cannula having proximal and distal points and a hub coupled to the needle cannula. The hub includes a flexible roof, or ball-and-socket arrangement, that permits the needle cannula to move about the centerline of the hub. The flexible roof can include one or more concentric ribs to enhance flexibility of the needle cannula about the centerline of the hub."

U.S. Pat. No. 3,994,295 discloses that, "An adapter device for mounting a hypodermic needle on a syringe barrel consists of two telescoped elements the outer of which is a casing or shell and the inner or which is a resilient tube bonded at opposite ends to a stem adapted for connection to the barrel and a needle mounting member seated over the end of the shell."

Additional background art includes Edwin Chan, Yuh-Fun Maa, Ph.D and David Overcashier; Manufacturing Consideration in Developing a Prefilled Syringe—Investigating the Effect of Headspace Pressure; American Pharmaceutical Review, May 8, 2012 and Appendix 3 Measurement of Leakage of Tuberculin Syringes; World Health Organization Monograph Series No. 12; BCG Vaccination, editors Lydia Edwards, Carroll Palmer and Knut Magnus; Tuberculosis Research Office World Health Organization Copenhagen; World Health Organization; Palais Des Nations, Geneva, 1953.

BRIEF SUMMARY OF THE INVENTION

According to an aspect of some embodiments of the invention, there is provided an assembly for aligning a cartridge interface of a drug delivery device to an access channel of a cartridge, the apparatus comprising: a collar having an opening sized and shaped for engaging the cartridge on opposing sides of the access channel; a cannula mounted to the collar; an tip region of the cannula extending into the access channel when the collar is engaged to the cartridge; a frame including a guide fitting to the cartridge to align and position the access channel with respect to the frame and a compliant support compliantly aligning and positioning the collar with respect to the frame the aligning and positioning the collar to engage the cartridge when the cartridge is aligned and positioned to the frame by the guide; the compliant support allowing movement of the collar preserving alignment of the cannula to the access channel upon misalignment of the access channel with respect to the frame.

According to some embodiments of the invention, the movement of the collar is elastic.

According to some embodiments of the invention, the misalignment of the cartridge is equal to a deviation tolerance of the positioning of the access channel with respect to the frame.

According to some embodiments of the invention, the preserving an alignment of the cannula is to within an alignment tolerance of the cannula to the access channel.

According to some embodiments of the invention, the compliance allows transaxial movement of the tip region of the cannula under a stress, the transaxial movement being more than a transaxial movement due to a flexibility of the frame under the stress.

According to some embodiments of the invention, the compliance allows transaxial movement of the tip region of the cannula under a stress, the transaxial movement being more than a transaxial movement due to a flexibility of the cannula under the stress.

According to some embodiments of the invention, the compliance allows transaxial movement of the tip region of the cannula more than a deviation tolerance of the positioning of the access channel by the guide.

According to some embodiments of the invention, preserving alignment of the cannula with the access channel is to within a deviation tolerance of a positioning of the cannula with respect to the access channel that is less than a transaxial deviation tolerance of the positioning of the access channel with respect to the frame.

According to some embodiments of the invention, a freedom of movement the collar with respect to the frame is greater than a deviation tolerance of positioning of the cannula in the access channel.

According to some embodiments of the invention, the guide includes a channel fitting to a body of the cartridge.

According to some embodiments of the invention, the channel includes an open end opposite the collar and wherein the cartridge slides through the open end into the channel until the cartridge engages the collar.

According to some embodiments of the invention, the collar includes an elastically expanding friction interface for the engaging to the cartridge.

According to some embodiments of the invention, the compliant support includes at least one member selected from the group consisting of a flexible mount, a pivoting support, and a support with a slack.

According to some embodiments of the invention, the assembly further includes: a base blocking movement of the cannula away from the cartridge in an axial direction.

According to an aspect of some embodiments of the invention, there is provided a method of supplying a drug to a delivery device comprising: compliantly supporting a collar including a cannula in a ready position on a frame of the drug delivery device; positioning a cartridge within a first deviation tolerance of a loaded position with respect to a frame; the positioning engaging an access channel of the cartridge to the collar when the cartridge is in the ready position; inserting an end of the cannula into the access channel; allowing movement of the collar with respect to the frame to comply with the loaded position of the cartridge to preserve an alignment of the end of the cannula with respect to the access channel to a second deviation tolerance less than the first deviation tolerance.

According to some embodiments of the invention, the allowing movement includes more transaxial movement of the end of the cannula than a movement due to a at least one element selected from the group consisting of a flexibility of the frame and a flexibility of the cannula.

According to some embodiments of the invention, a freedom of movement the collar with respect to the frame is greater than a deviation tolerance of positioning of the cannula in the access channel.

According to some embodiments of the invention, the method further comprises: blocking movement of the cannula away from the cartridge in an axial direction.

According to an aspect of some embodiments of the invention, there is provided a method of preventing leakage from a cartridge of a drug delivery device comprising: providing a cartridge fitting supported on a housing of the delivery device and a cannula mounted to the fitting; piercing the septum with the cannula; rigidly engaging the fitting to the cartridge; allowing the fitting to move along with the cartridge with respect to the housing such that the cannula moves with the septum; wherein the moving of the cannula with the septum provides for inhibiting leaks caused by movement of the septum with respect to the cannula.

According to some embodiments of the invention, the method fitting is supported on the housing to limit a freedom of movement of a tip of the cannula with respect to the housing along an axis of the septum and wherein the allowing of the fitting to move with respect to the housing provides a freedom of movement of a tip of the cannula in a direction transaxial to the septum the transaxial freedom of movement being greater than the axial freedom of movement. Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF THE INVENTION

Figure 1:
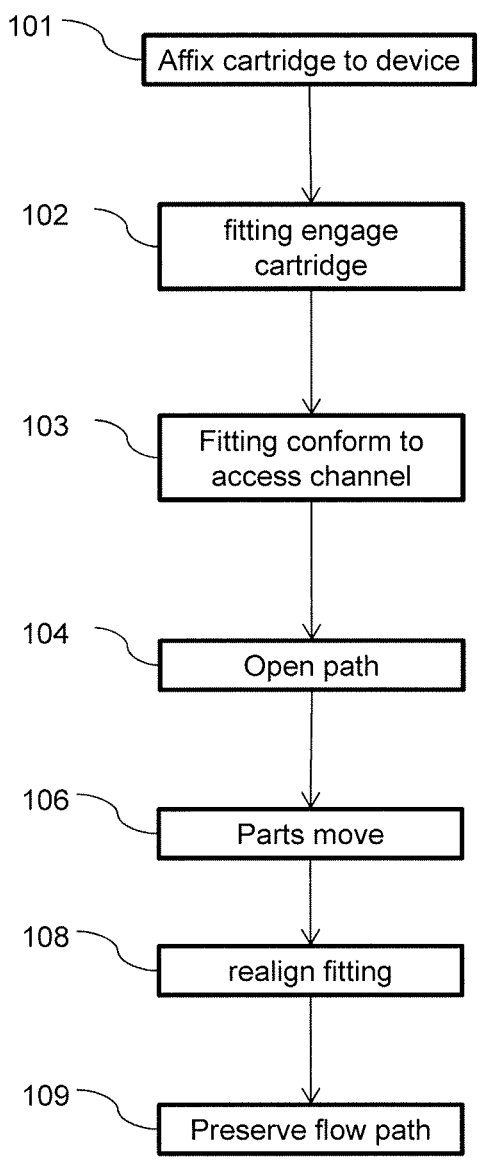
FIG. 1 is a flow chart illustration of a method of aligning a coupling to an access channel of a drug cartridge in accordance with an embodiment of the present invention.

The present invention, in some embodiments thereof, relates to a coupling alignment system for a drug cartridge and, more particularly, but not exclusively, to a collar for aligning a cannula with a septum of a drug cartridge.

An aspect of some embodiments of the present invention relates to a compliant support that flexibly positions a cartridge fitting in a drug delivery device. Optionally the support may position the fitting to engage the cartridge when the cartridge is affixed to the device. In some embodiments, the support may be compliant to allow the fitting to move and/or comply with the position of a drug cartridge even when there is misalignment between the cartridge and the device. In some embodiments, the fitting may include a coupling connecting the drug cartridge to a fluid path of the delivery device. For example, the fitting may keep the coupling precisely positioned and/or aligned to the cartridge. Precise alignment may avoid leading between the cartridge and the coupling and/or avoid damage to the cartridge and/or the coupling.

In some embodiments, a cartridge may include a narrow neck with an access channel sealed by a septum. The cartridge fitting may include a collar that engages the narrow neck and a cannula that punctures the septum and/or couples the cartridge to a fluid path for discharge of the drug. The cartridge is optionally positioned in a guide channel in a housing of the delivery device. The collar is optionally positioned at the end of the guide channel on compliant supports such that when the cartridge is fully inserted into the guide channel, the collar engages the cartridge. Optionally, the collar can move to align itself to the neck of the cartridge. For example the collar may holds the cannula precisely aligned with the access channel of the cartridge even when the cartridge is not precisely aligned with the housing of the delivery device.

In some embodiments, a drug delivery device may include a cartridge guide orienting and/or positioning a cartridge with respect to a frame according to a first machining tolerance. The cartridge fitting engage the cartridge and/or retain a coupling connected to an access channel of the cartridge with a second tolerance more precise than the first tolerance.

In some embodiments, the coupling may connect the cartridge to an internal fluid path in the drug delivery device. The connection between the coupler and the fluid path may include a flexible element. The flexible element may comply to movement of the coupling. The flexibility of the fluid path may in some embodiments reduce the force required to move the coupling and/or the stress on the coupling as it moves. Optionally, a portion of the fluid path may be tethered to the cartridge fitting (for example by a clamp). The tethered portion of the fluid path may move with the fitting. Tethering a portion of the fluid path to the fitting may further reduce forces on the coupling and/or on the interface between the drug delivery device and the cartridge.

In some embodiments the precision of positioning of the access channel of the cartridge with respect to the housing may have deviation tolerance (allow deviation from the specified position) ranging for example between 0.5 to 5 mm. Alternatively or additionally the deviation tolerance of the position of the access channel with respect to the housing may range between 0 to 0.5 mm and/or 0.5 to 2 mm and/or 2 to 5 mm and/or 5 to 10 mm and/or 10 to 16 mm. The deviation tolerance of orientation of the access channel with the housing may range for example between 0 to 1 degrees. Alternatively or additionally, the deviation tolerance of orientation of the access channel with the housing may range for example between 0 to 0.3 degrees and/or between 0.3 to 1 degree and/or between 1 to 3 and/or between 3 to 10 degrees. For example, when the cartridge is engaged with the fitting, the deviation tolerance of positioning of the access channel of the cartridge with respect to the coupling may range for example between 0. to 0.6 mm in all directions. Alternatively or additionally the deviation tolerance of positioning of the access channel of the cartridge with respect to the coupling may range for example between 0.1 to 0.3 mm and/or from 0.3 to 0.6 mm and/or between 0.6 to 2 mm. the deviation tolerance of orientation of the access channel with the coupling may range for example between 0 and 3 degrees. Alternatively or additionally, the deviation tolerance of orientation of the access channel with the coupling may range for example between 00.3 degrees and/or between 0.3 and 1 degree and/or between 1 and 3 degrees and/or between 3 and 10 degrees.

In some embodiments the coupling is flexibly mounted to the cartridge fitting and/or housing of a medical device. For example movements of the coupling may accommodate flexing and/or movement and/or mismatch between the fitting and/or coupling and/or cartridge and/or housing reducing stress on the interface between the cartridge and the coupling.

In some embodiments, the flexibility may allow freedom of movement of the alignment system that is directionally dependent. For example, the tip of the cannula may have a large sideways freedom of movement (for example the tip may be free to move transaxially and/or laterally a distance as much as 0.6 mm under a side load of 6 N or less) and/or have a smaller or greater freedom of movement in the distal direction (for example the tip may be free to move transaxially and/or laterally a distance ranging between 0.2 to 0.5 and/or 0.5 to 0.7 mm and/or 0.7 to 2 mm under a side load of 6 Newton (N) and/or under a side load ranging between 2 to 5 N and/or between 5 to 10 N and/or between 10 to 20 N). For the sake of the current disclosure, a transaxial movement may be defined as a movement perpendicular to the axis an object before the movement. For example a linear movement perpendicular to an axis is transaxial. For example, under the above definition, rotation that changes the orientation of an axis causes transaxial movement at points distant for the axis of rotation. For example, a base may be provided distal to the cannula, bracing the cannula and/or blocking distal movement of the cannula. Bracing the fitting and/or the cannula may facilitate engagement of said cartridge by said collar. For example, affixing the cartridge to the guide may cause the collar to engage the cartridge. In some embodiments transaxial movement may be with respect to the cannula and/or the septum and/or the access channel of the cartridge and/or the cartridge.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

1. Method of Supplying a Drug

Referring now to the drawings, FIG. 1 illustrates a method of supplying a drug to a drug delivery device. The drug may be supplied to the device through a coupling (for example a cannula) connected to a drug cartridge. In some embodiments, the delivery device includes cartridge fitting that aligns the coupling to the cartridge with a high precision. Optionally, the fitting is positioned on the device to engage the cartridge when the cartridge is affixed to the device. In some embodiments, the cartridge may be affixed to the delivery device with a low precision (for example with a large deviation tolerance) whereas the coupling may fit to the cartridge with a high precision (for example a small tolerance for deviation of alignment). Optionally, the cartridge fitting is supported on the delivery device to conform to the position of the cartridge. For example if the cartridge moves during use, the cartridge fitting may move with the cartridge, keeping the coupling aligned with the access channel. In some embodiments, the fitting may orient the cartridge rotationally around its axis. Alternatively or additionally, in some embodiments, the cartridge may not be fixed in the rotational orientation around its axis.

In some embodiments a drug cartridge may be affixed 101 to a delivery device. A cartridge fitting may be positioned to engage 102 the cartridge when the cartridge is affixed 101 to the device.

For example the cartridge may be slid into a guide channel of the device. The fitting optionally is positioned at the end of the guide to engage the cartridge when it is fully inserted. For example the fitting may include an expanding friction fitting that grasps a distal end of the cartridge as it is inserted into the guide channel. For example, the cartridge may have an access channel sealed by a septum on the distal end thereof. In various embodiments, the septum may be slightly misaligned with the housing of the device. For example misalignment may result from deviation in positioning of the septum with respect to the body of the cartridge and/or deviation in positioning of the channel with respect to the housing and/or deviation in positioning of the cartridge with respect to the channel and/or from deviation of the position of the channel with respect to the cannula and/or due to unbalanced forces when inserting the cartridge into the channel and/or other factors.

In some embodiments, the injector may include a self aligning cartridge fitting. For example, the fitting may grasp and/or guide the distal end of the cartridge and/or align itself to conform 103 to the position of the septum. For example, the cartridge fitting may grasp the cartridge near the location of the access channel and/or at a location where the spatial location with respect to the access channel is at a relatively higher precision (for example has a smaller deviation tolerance). Optionally the cartridge fitting may conform to the location of the cartridge and/or adjust itself to properly position the coupling with respect to the access channel and/or adjust itself to compensate for deviation and/or movement of various parts of the coupling system. In some embodiments' movement of the cartridge fitting preserves alignment between the coupling and the access channel.

In some embodiments, a path may be opened 104 between the drug delivery device and the cartridge. Optionally, the path may be used to supply the drug to the delivery device. For example opening 104 a path between the cartridge and delivery device may include opening 104 a fluid flow path allowing flow of a liquid drug from the cartridge to the delivery device. For example the fluid path may be supplied from the access channel of the cartridge to the coupling of the delivery device. For example, the coupling may include a cannula which may be pushed through a septum of the access channel.

In some embodiments, parts of the injector may move 106 after the path is opened 104 between the delivery device and the cartridge. For example, a plunger may be pushed into the cartridge to push out the contents. The force of the plunger may cause movement (for example movement of the cartridge and/or the access channel with respect to the housing). Optionally, the cartridge fitting may realign 108, for example by moving along with the cartridge and/or the access channel. Realigning the cartridge fitting may preserve 109 the integrity of the flow path and/or preserve 109 the flow path in an open state. In some embodiments, preserving 109 the flow path may include preserving 109 alignment between the coupling and the access channel. In some embodiments, preserving integrity of a flow path may prevent leakage of the contents of the cartridge.

2. States of an Alignment System

Figure 2:
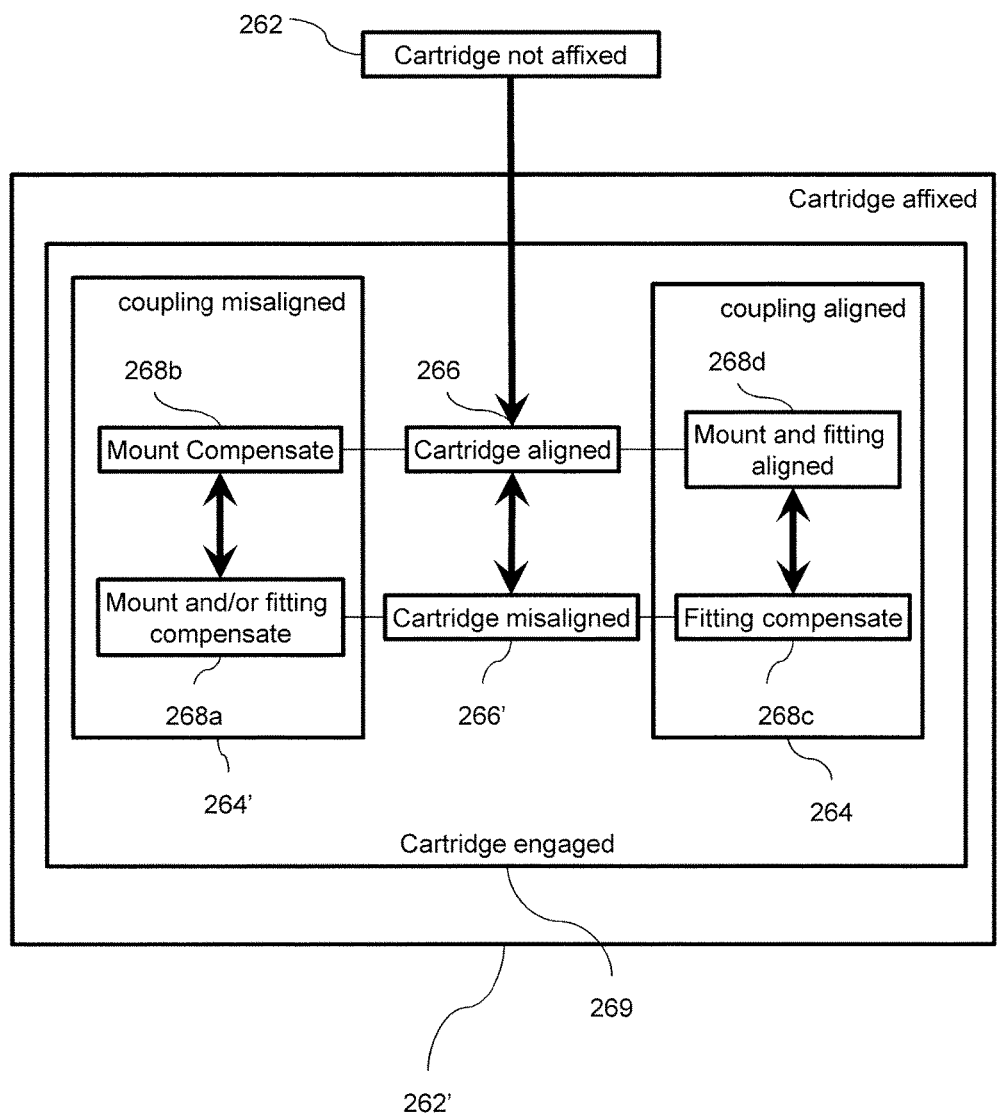
FIG. 2 is a state diagram of a system for aligning a coupling to an access channel of a drug cartridge in accordance with an embodiment of the present invention.

FIG. 2 is a state diagram illustrating states of an alignment system in accordance with an embodiment of the current invention. Optionally an alignment system may include a flexible mount for a fluid path coupling and/or a movable cartridge fitting for holding a coupling to an access channel of a cartridge. Optionally, the mount and/or fitting may compensate for misalignments of one or more parts of the fluid train. In some embodiments, compensation by the mount and/or the cartridge fitting preserves a fluid path between the delivery device and the cartridge even in various states of movement and/or misalignment of the cartridge and/or the fitting and/or the coupling.

In some embodiments, a cartridge coupling system of a drug delivery device and/or a cartridge of the device may be affixed 262' and/or may be properly aligned 266 without compensation. Affixing of the cartridge to the delivery device may include for example insertion into a guide in the housing of the device and/or engagement 269 with the cartridge fitting. For example, a cartridge may be aligned 266 to a housing of the device and/or a coupling may be aligned 264 to the cartridge fitting of the device and/or the cartridge fitting may be aligned 268*d* with the housing of the device.

In some embodiments, when a coupling is affixed 262' to a cartridge guide, a misalignment of the cartridge may be compensated for by a coupling system. For example, the cartridge may engage 269 a cartridge fitting which may realign 268*a*, 268*c* to compensate for misalignment of the cartridge. Some examples of imprecision and/or deviation for which a flexible fitting and/or mount compensates may include imprecision in manufacturing of the cartridge, deviation in placement of the cartridge in the delivery device, deviation in positioning of the coupling with respect to the cartridge fitting, imprecision in manufacturing of the coupling, imprecision in manufacturing of the housing of the delivery device, deviation in position of the cartridge fitting with respect to the housing deviation in positioning of the guide for the cartridge etc.

In some embodiments, flexing the mount of a coupling may compensate 268*b* for a misalignment 264' of the coupling with the cartridge fitting (for example due to manufacturing imprecision of the coupling and/or the fitting). For example the cartridge fitting optionally remains aligned with the access channel of the cartridge.

In some embodiments, flexing of a coupling mount may compensate 268*a*, for a misalignment 266' and/or movement of a cartridge with respect to a housing of the drug delivery device (for example when the coupling is flexibly mounted to the cartridge fitting). Alternatively or additionally, realignment of a cartridge fitting may compensate 268*a*, 268*c* for a misalignment 266' and/or movement of a cartridge with respect to a housing of the drug delivery device (for example in an embodiment where the coupling is rigidly mounted to the cartridge fitting and/or in an embodiment where the coupling is flexibly mounted to the cartridge fitting).

In some embodiments, a drug cartridge may be supplied unaffixed 262 from a drug delivery device. Optionally or alternatively, the cartridge and the device may be integrally manufactured.

3. Alignment System

Figure 3:
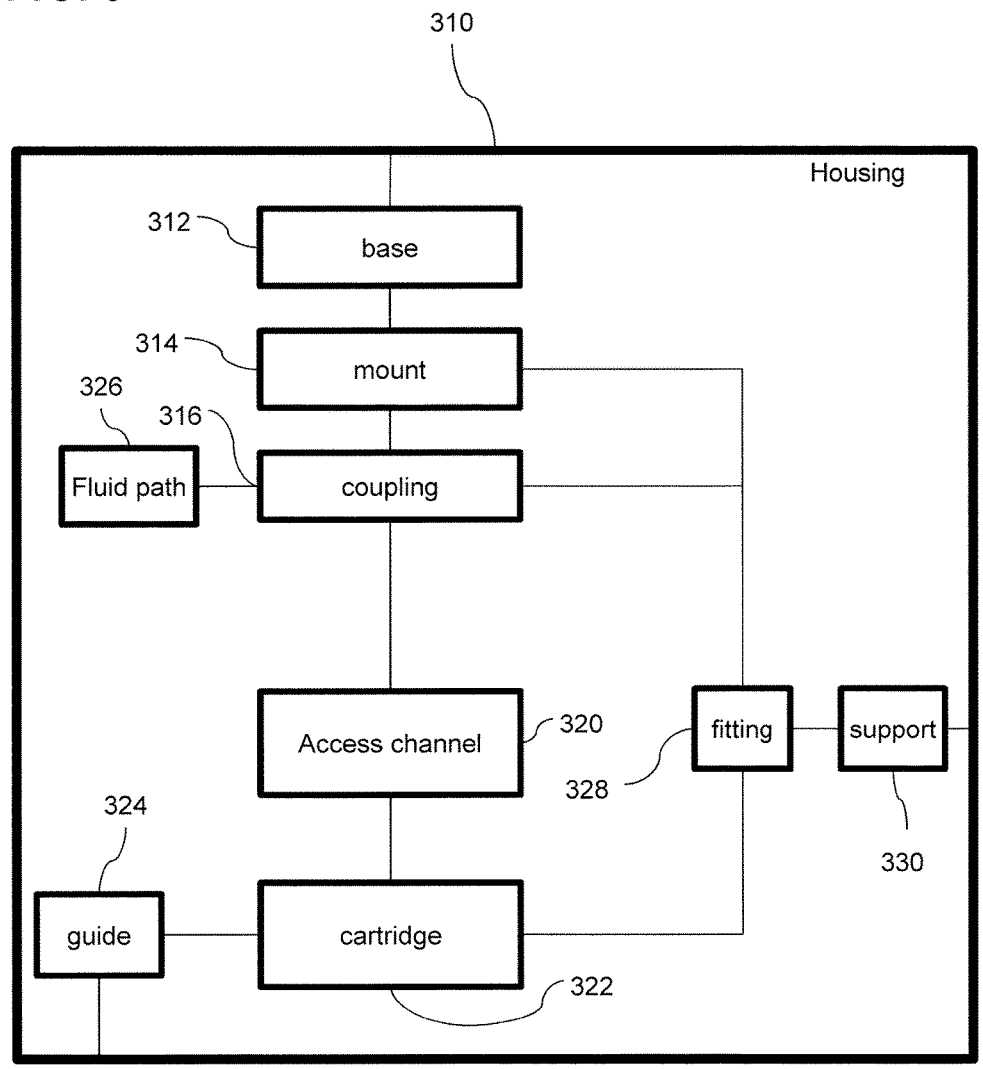
FIG. 3 is a state block diagram of a system for aligning a coupling to an access channel of a drug cartridge in accordance with an embodiment of the present invention.

FIG. 3 is a block diagram illustrating a system for compensating for misalignment between a coupling and an access channel in accordance with an embodiment of the current invention. In some embodiments, a housing 310 of a drug delivery device includes a guide 324 for positioning a drug supply cartridge 322 and/or a base 312 bracing a coupling 316 and/or a fitting 328 against axial movement. Coupling 316 optionally provides material transport between cartridge 322 and the drug delivery device for example through an internal fluid path 326 of the delivery device. A misalignment between coupling 316 and cartridge 322 may cause a disconnection and/or a blockage and/or a leakage. For example, misalignment may be caused by defects in some or all of the parts and/or rough handling of the device. A misalignment compensation system optionally includes freedom of movement of one or more parts to compensate for the misalignment. For example the system may include fitting 328 which engages cartridge 322. Fitting 328 may hold coupling 316 aligned to cartridge 322. Optionally fluid path 326 may contain flexible and/or movable components.

In some embodiments, fitting 328 may be movably mounted to frame (for example a housing 310 of the drug delivery device). For example, fitting 328 may be connected to housing 310 by a flexible base 312 and/or by a pivot support 330. Flexible base 312 and/or a pivot support 330 may retain fitting 328 in a ready position and/or allow compensatory movement of fitting 328 with respect to housing 310 for example to preserve alignment between cartridge 322 and fitting 328. In the ready position, fitting 328 may engage cartridge 322 when cartridge 322 is affixed to housing 310 in a predefined affixed position. The affixed position may predefined with a deviation tolerance.

In some embodiments, fitting 328 may be engaged to cartridge 322 near an access channel 320 thereof. The fluid path optionally crosses between access channel 320 and coupling 316. In some embodiment fitting 328 may preserve alignment between coupling 316 and access channel 320 of cartridge 322. Optionally or additionally, coupling 316 may movable attached to housing 310 and/or fitting 328. For example, coupling 316 may be attached to housing 310 and/or to cartridge fitting 328 via flexible mount 314. Flexible mount 314 optionally allows compensatory movements of coupling 316 and/or realignment of coupling 316 and cartridge 322. The flexibility of the mount may, in some embodiments, give a greater freedom of movement to the coupling than flexibility of other parts of the system (for example the guide and/or a frame and/or a housing of the device).

In some embodiments, the design of base 312 and/or support 330 may allow movement of fitting 328 and/or coupling 316 more in one direction than in another. For example, fitting 328 and/or coupling 316 may be allowed to move relatively freely perpendicular to guide 324 and/or to rotate with respect to guide 324. Movements toward or away from guide 324 in the direction of a longitudinal direction may for example be more limited. For example, liming longitudinal movement of fitting 328 and/or coupling 316 may make it easier to connect the access channel 320 to coupling 316 and/or engage a fitting (for example a collar 428) to cartridge 322, for example when inserting cartridge 322 into the device.

In some embodiments, cartridge 322 may include an access channel 320 near a distal end thereof. For example, access channel 320 may include a neck sealed by a septum. Optionally the septum is oriented laterally (e.g. transaxial to the cannula e.g. perpendicular to the cannula and/or perpendicular to a longitudinal axis of the cartridge running for example from the distal end to the proximal end of the cartridge).

In some embodiments cartridge 322 is inserted longitudinally into the proximal end of a guide 324 channel housing 310 of the drug delivery device. Cartridge fitting 328 may include, for example a cup and/or collar and/or a gripping expander sleeve that attaches (for example by a flexible snap) to the distal end of cartridge 322. Coupling 316 may include, for example, a cannula and/or a hollow needle. Cartridge fitting 328 optionally retains coupling 316 oriented longitudinally parallel to and/or coaxial to guide 324 channel and/or near the proximal end of the guide 324 channel. In some embodiments, as cartridge 322 is inserted, it contacts cartridge fitting 328 and/or is pushed into the fitting 328. Fitting 328 optionally aligns itself to the cartridge 322 and/or engages cartridge 322 (for example by snapping onto the distal end of the cartridge 322). Fitting 328 optionally retains the cannula oriented substantially parallel and/or coaxial to access channel 320 and/or oriented substantially parallel to a longitudinal axis of cartridge 322. As the cartridge 322 is pushed into fitting 328, the cannula may optionally puncture the septum. After the puncturing of the septum, the hollow of the cannula may form a flow path from the inside of cartridge 322 through the septum and/or into internal flow path 326 of the drug delivery device. Movements of the cartridge 322 with respect to guide 324 and/or housing 310 are optionally compensated by compliant movements of cartridge fitting 328. For example compensating movements of fitting 328 with respect to guide 324 may accommodate and/or compensate for and/or comply to movement and/or deviation and/or mismatch of cartridge 322 and/or guide 324. Optionally the compensating movements may limit and/or substantially avoid stress on the interface between cartridge 322 and coupling 316 (for example limiting stress on the septum and/or tearing and/or leaking of the septum). For example, the stress on the interface between the cannula and the septum may be preserved below a leak threshold force. A leak threshold force may be defined, for example, as a stress on a puncture site of a septum large enough to produce a leak greater than 0.05 ml under working conditions. Alternatively or additionally the test leak threshold force may be defined under a test pressure for example ranging between 1 to 5 $kg/cm^2$ and/or between 5 to 6 $kg/cm^2$ and/or between 6 to 12 $kg/cm^2$. Alternatively the leak volume may range for between 0.01 to 0.05 ml and/or between 0.05 to 0.1 ml and/or between 0.1 to 0.2 ml and/or between 0.2 to 0.5 ml and/or between 0.5 to 1 ml. The leak volume may be defined over a given time (for example the volume may leak out over a time ranging between 0 and 60 seconds and/or between 1 to 10 minutes and/or between 10 minutes to an hour and/or between an hour to a day). A leak threshold strain may be defined for example as a quantity of movement of a cannula puncturing a septum that causes leaking between the cannula and the septum, for example leakage of more than 0.05 ml under working conditions. Alternatively or additionally the test leak threshold strain may be defined under a test pressure for example ranging between 1 to 5 $kg/cm^2$ and/or between 5 to 6 $kg/cm^2$ and/or between 6 to 12 $kg/cm^2$. Alternatively the leak volume may range for between 0.01 to 0.05 ml and/or between 0.05 to 0.1 ml and/or between 0.1 to 0.2 ml and/or between 0.2 to 0.5 ml and/or between 0.5 to 1 ml.

4. Embodiment for Piercing a Septum of a Cartridge

Figure 4:
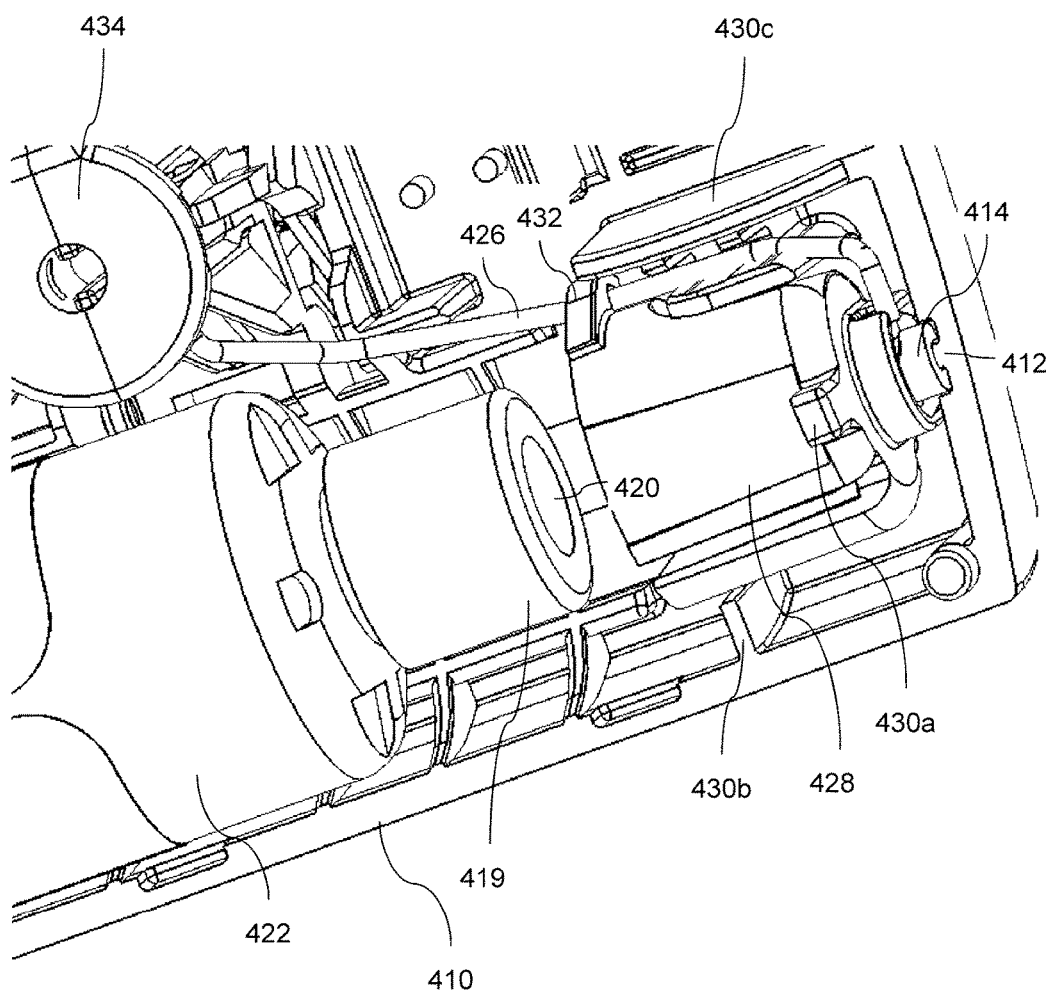
FIG. 4 is a dorsal perspective view of the distal end of a drug cartridge and a system for aligning a coupling to an access channel of the drug cartridge in accordance with an embodiment of the present invention.

FIG. 4 is a close up dorsal perspective view of a system for aligning a coupling and an access channel of a drug delivery device in accordance with an embodiment of the present invention. In the exemplary embodiment of FIG. 4, the coupling system of a drug delivery device includes a cannula 516 (for example see FIG. 5). In the exemplary embodiment of FIG. 3, the neck of the cartridge includes a thin access channel 621 (see for example FIG. 6) sealed by a septum 420. In the exemplary embodiment of FIG. 3, the cartridge fitting includes a collar 428. Cannula 516 is engaged to collar 428 by a mount 414. Optionally mount 414 is flexible. Alternatively or a additionally mount 414 may be rigid. The distal end of mount 414 is optionally supported on housing 410 of the drug delivery device by a pivoting connection to a base 412. In the embodiment of FIG. 4, collar 428 is movably supported in a ready position on housing 410 of the drug delivery device by one or more supports 430a, 430b, 430c, 430d (for example see FIG. 5) and 430e (for example see FIG. 7). For example, in the ready position, the opening of collar 428 is directed toward a guide channel 424 so that when cartridge 422 is inserted into the guide channel, the distal end of cartridge 422 is engaged by collar 428.

In some embodiments, a coupling and/or a fitting may move more freely in one direction than another. For example, base 412 limits longitudinal movement of cannula 516 and/or collar 428. For example, longitudinal movement of cannula 516 may be limited to a range between 0 and 0.1 mm. Alternatively or additionally longitudinal movement of cannula 516 may be limited to a range between 0.1 to 0.2 mm and/or between 0.2 to 0.5 mm. For example, longitudinal movement of collar 428 may be limited to a range between 0 and 0.1 mm and/or between 0.1 to 0.2 mm and/or between 0.2 to 0.5 mm. In some embodiments, limiting longitudinal movement collar 428 may make it easier to insert cartridge 422 (and/or a collar adapter 419 of cartridge 422) into collar 428. In some embodiments, limiting longitudinal movement of cannula 516 may make it easier to insert cannula 516 into septum 420. For example in the embodiment of FIG. 4 freedom of lateral movement of the proximal end of collar 428 may range for example between 0.1 mm to 0.4 mm. In some embodiments, pivoting of mount 414 around base 412 and/or slack around supports 430a-d and/or pivoting around supports 430a-d may allow lateral translational movement of the proximal end of collar 428 ranging between 0 to 0.1 mm and/or 0.1 mm to 0.4 mm and/or 0.4 to 1 mm. For example in the embodiment of FIG. 4 freedom of rotation of collar 428 may range between 0.5 and 2 degrees. In some embodiments rotation of collar 428 range between 0.1 to 0.5 degrees and/or 0.5 and 2 degrees and/or 2 to 5 degrees. For example an optional slack 576d between support 430d and the inner wall of housing 410 may allow vertical movement of collar 428. For example an optional slack 576b between support 430d and collar 428 may allow horizontal movement of collar 428. For example an optional slack 676c (for example see FIG. 6) between support 430c and collar 428 may allow horizontal movement of collar 428. Optionally, transaxial movement may be defined with respect to cannula 516, collar 428, channel 621 and/or septum 420. For example, in the exemplary embodiment of FIG. 4 the axes of cannula 516, collar 428, channel 621 and septum 420 are substantially parallel. Alternatively or additionally, in some embodiments, the axes of cannula 516, collar 428, channel 621 and septum 420 may be non-parallel.

In some embodiments, collar 428 may include a gripping expander sleeve. The expander sleeve optionally grips the distal end of the cartridge. Optionally, in the embodiment of FIG. 4 the length of the sleeve may range for example between 8 to 9 mm. In some embodiments, the sleeve may have a length for example ranging between 2 to 8 mm and/or 8 to 9 mm and/or 9 to 15 mm. Optionally, in the embodiment of FIG. 4 the length of the sleeve may range for example between 8.4 to 8.6 mm. In some embodiments, the sleeve may have a diameter ranging between 6 to 8.4 mm and/or 8.4 to 8.6 mm and/or 8.6 to 12 mm. In some embodiments the opening of the expander sleeve faces proximally. Optionally the coupling may include cannula 516 directed proximally into the expander sleeve. For example, in the embodiment of FIG. 5, cannula 516 may project a distance ranging between 5 to 6 mm. In some embodiments, the cannula may project a distance ranging between 2 to 5 mm and/or 5 to 6 mm and/or 6 to 10 mm and/or 10 to 20 mm proximally into the expander sleeve. For example cannula 516 may include a hollow bore needle ranging between 25 and 30 gauge. Alternatively or additionally a cannula may range between 15 to 25 gauge and/or between and/or 30 to 40 gauge. Collar 428 may be made for example of molded Polycarbonate. Mount 414 may be a hard plastic or resin for example Polycarbonate. Alternatively mount 414 may be made of a more flexible material for example an elastomer, for example TPE. For example the length of the axis channel (for example channel 621 for example as illustrated in FIG.

Figure 6:
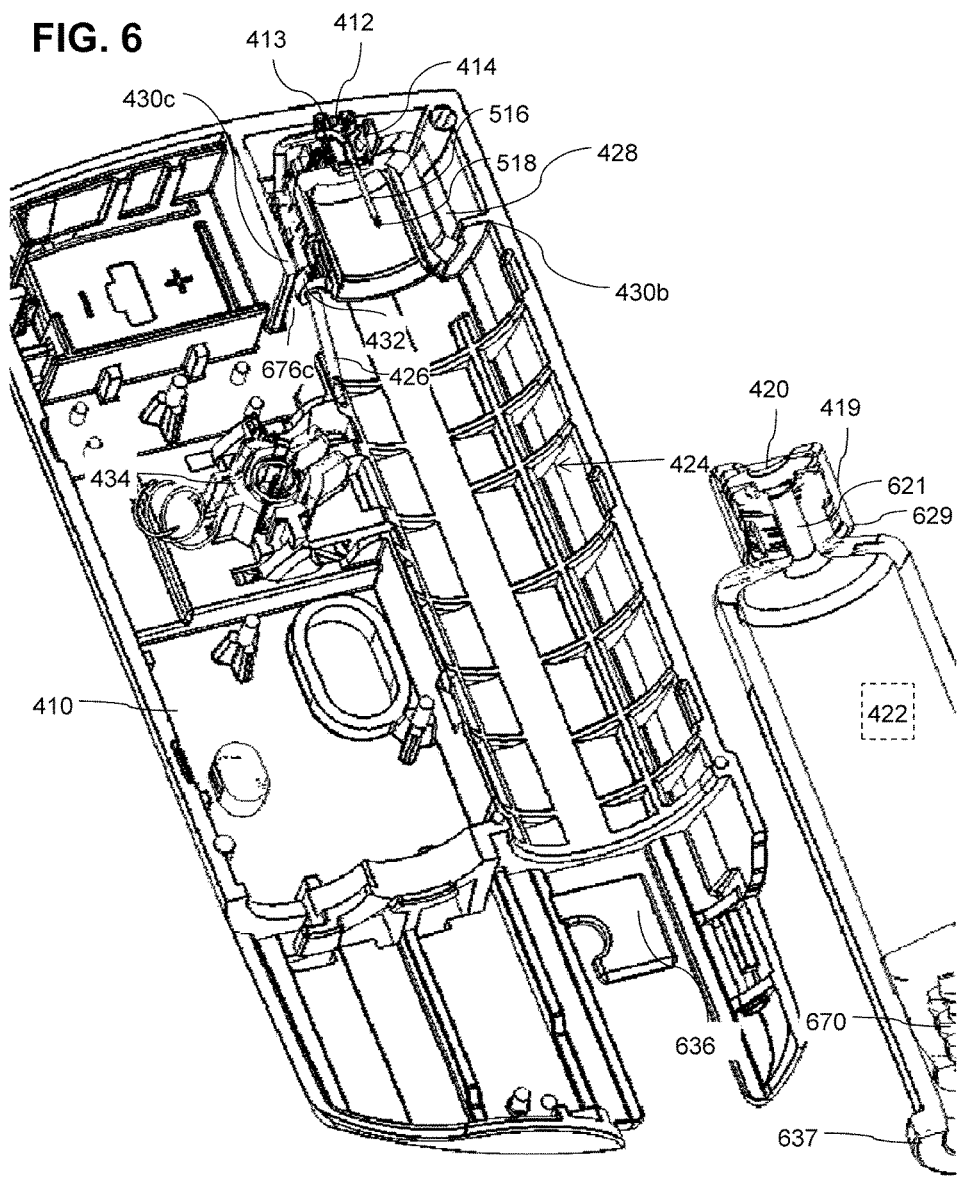
FIG. 6 is a dorsal cross sectional (along line A-A' of FIG. 5) view of a system for aligning a coupling to a channel of a drug cartridge installed in a delivery device in accordance with an embodiment of the present invention.

6) may range between 8.6 to 8.9 mm. For example the inner diameter of the axis channel (for example channel 621 for example as illustrated in FIG. 6) may range between 2 to 4 mm. In some embodiments, the length of the axis channel may range for example between 5 to 15 mm. In some embodiments, the inner diameter of the axis channel may range for example between 1 to 3 mm and/or between 3 to 5 mm and/or between 5 to 10 mm.

In some embodiments, an internal fluid path connecting the coupling to a delivery subassembly may include a flexible section. For example, an internal fluid path of the embodiment of FIG. 4 connects a coupling to a patient needle insertion assembly 434. The fluid path optionally includes a flexible tube 426. In some embodiments, the flexibility of tube 426 allows the couple to move without large resistance from and/or breakage of the fluid path. Optionally collar 428 includes a clip 432 that causes the distal portion of tube 426 to move in conjunction with collar 428. Optionally when collar 428 moves, clip 432 protects the coupling and/or the interface between cartridge 422 and the delivery device from forces produced by movement of tube 426. Optionally the tube may be made for example of Silicone or Tygon. The length of the tube may range for example between 30 and 50. The inner diameter of the tube may range for example between 0.25 and 0.5.

Figure 5:
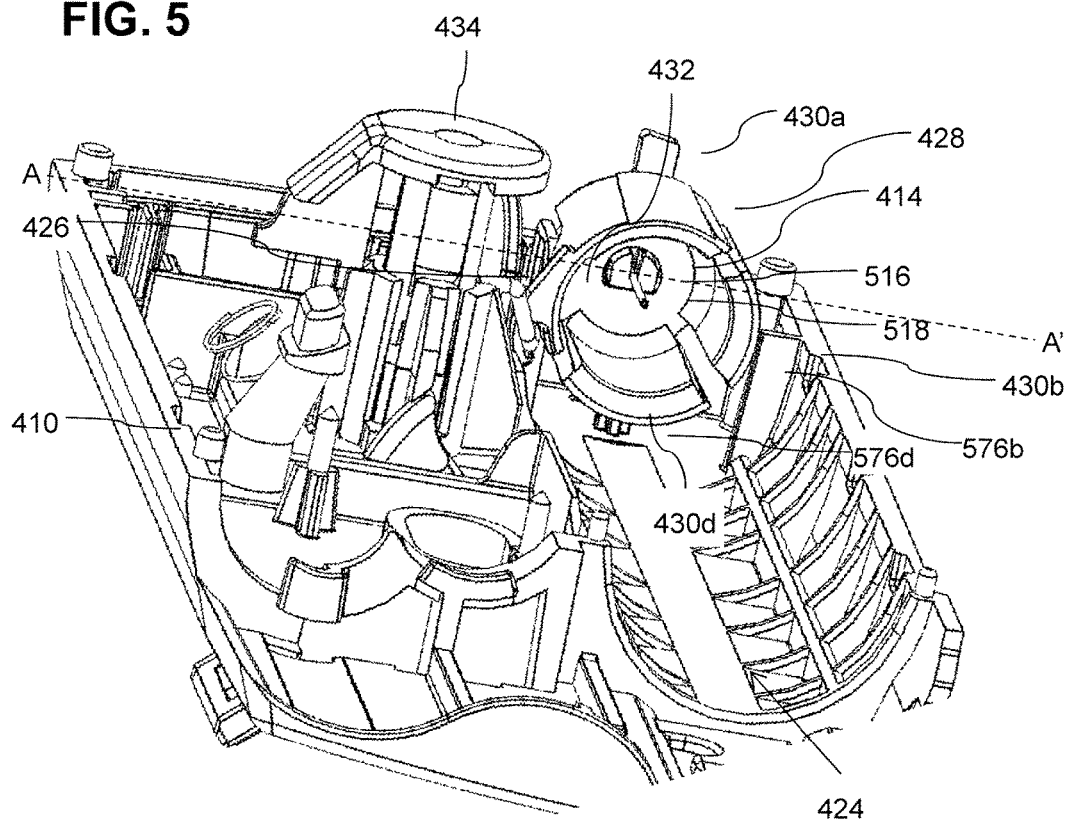
FIG. 5 is a proximal perspective view of a system for aligning a coupling to an access channel of a drug cartridge installed in a delivery device in accordance with an embodiment of the present invention.

FIG. 5 is a proximal perspective view of a system for aligning a coupling and an access channel of a drug delivery device in accordance with an embodiment of the present invention. In FIG. 5, the proximal side of mount 414 can be seen protruding through a hole in the distal base of collar 428. The proximal portion of cannula 516 is seen protruding proximally from mount 414. Optionally the proximal end of cannula 516 includes a sharpened tip 518. Optionally mount 414 is rigidly connected to collar 428. For example, as collar 428 moves to accommodate misalignment of cartridge 422, mount 414 and/or cannula 516 move accordingly. In some embodiments, mount 414 is flexible. Flexibility of mount 414 optionally adds another degree of freedom to the system. For example, flexibility of mount 414 may reduce forces on the interface between the delivery device and the cartridge (for example septum 420) caused by bending of cannula 516 and/or misalignment of mount 414 and housing 410 and/or misalignment of mount 414 and collar 428 and/or misalignment of septum 420 and adapter 419.

In some embodiments, a cartridge fitting may be formed to direct movements of the cartridge and/or fitting to compensate and/or align together. For example collar 428 includes a beveled opening so that as cartridge is inserted longitudinally into guide channel 424 and/or pushed into engagement with collar 428, the distal end of cartridge 422 and/or the proximal end of collar 428 are urged into alignment as they approach the engaged position. For example, as cartridge 422 slides into a locked position in collar 428 the beveled opening of the rotates urges collar 428 and cartridge 422 into a common longitudinal axis (for example by rotating collar 428 with respect to housing 410 and/or guide channel 424. Alternatively or additionally, the collar may be formed with a straight opening and/or the cartridge may have a beveled end.

In some embodiments, supports may movably align a cartridge fitting to a drug delivery device. For example, supports 430a and 430d are rigidly connected to collar 428. Supports 430a and 430d are optionally braced against the upper and lower sections of housing 410 but not rigidly connected thereto (the upper section 810 of housing 410 is illustrated, for example in FIG. 8). For example, supports 430a and/or 430d and/or collar 428 may pivot around the point where supports 430b and/or 430c rest on housing 410. Alternatively or additional supports 430a, d may slide along the inner surface housing 410. For example, supports 430b and 430c are rigidly connected to housing 410. In the exemplary embodiment, supports 430b and 430c buttress collar 428 (limiting its lateral movements) but are not rigidly connected thereto. Optionally, a slack (for example a space between collar 428 support 430b and/or 430c and/or a space between housing 410 and/or upper housing section 810 and support 430a and/or 430d) allows a limited freedom of movement, for example ranging between 0.1 mm and 0.4 mm to collar 428. In some embodiment the freedom of movement of a collar may range between 0.0 to 0.1 mm and/or between 0.1 to 0.4 mm and/or between 0.4 to 1 mm.

FIG. 6 is a dorsal cross sectional view (cut along a horizontal plane crossing line A-A' of FIG. 5) of a system for aligning a coupling to a channel of a drug cartridge installed in a delivery device in accordance with an embodiment of the present invention. In some embodiments, cannula 516 may include a bent needle, a proximal side of which couples to cartridge 422 (for example by piercing septum 420) and a distal side of which is connected to an internal fluid path (for example flexible tube 426) and/or to an output assembly such as Patient needle assembly 434. Mount 414 optionally includes a curved channel 413 through which passes the bent portion of cannula 516. Optionally, cannula 516 may be bent between 80 and 100 degrees and/or between 60 and 120 degrees and/or between 30 and 150 degrees.

The cross section view of cartridge 422 illustrates for example a narrowed neck of an access channel 621 of cartridge 422. An exemplary plunger 670 is illustrated near the proximal end of cartridge 422. Cartridge 422 optionally includes a distal flange 637.

FIG. 6 illustrates an optional locking latch 636. Latch 636 optionally locks cartridge 422 into guide channel 424. For example latch 636 blocks outward movement of a flange 637 on the proximal end of cartridge 422. Additionally or alternatively, collar 428 may grasp cartridge 422 near septum 420. For example collar 428 may include a snap and/or an interference element that locks for example onto a ledge 629 on the distal portion of cartridge 422.

Figure 7:
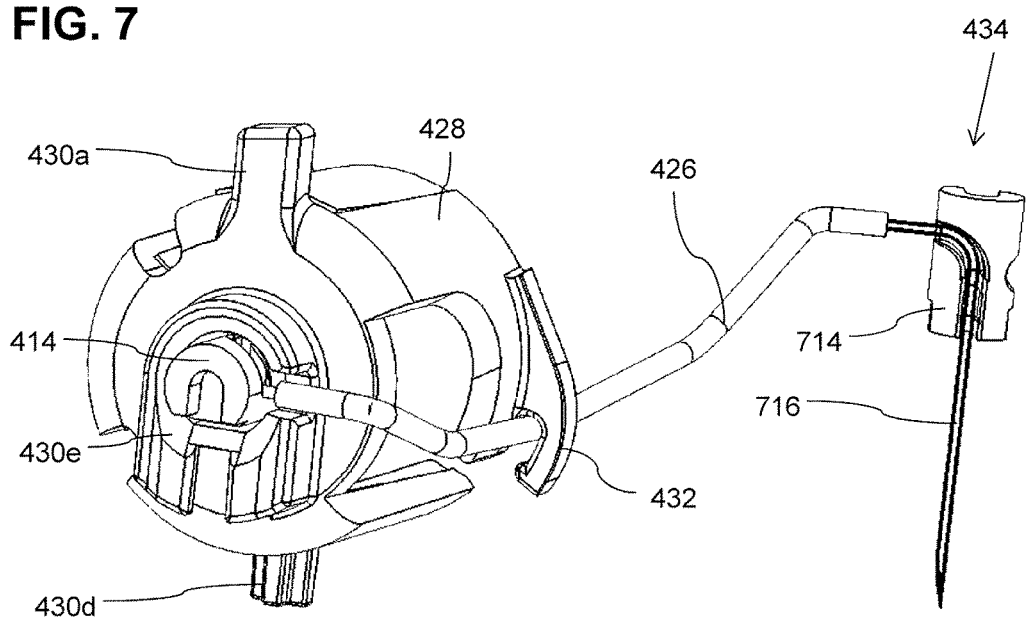
FIG. 7 is a distal perspective view of a system for aligning a coupling to a channel of a drug cartridge in accordance with an embodiment of the present invention.

FIG. 7 is a distal view of an alignment system in accordance with an embodiment of the current invention. FIG. 7 illustrates a further optional support 430e that pivotally connects collar 428 to base 412. FIG. 7 further illustrates details of needle insertion assembly 434 which optionally includes a bent needle 716 (for example for insertion into a patient) connected to tube 426 and/or a mount 714 with a curved channel.

Figure 8:
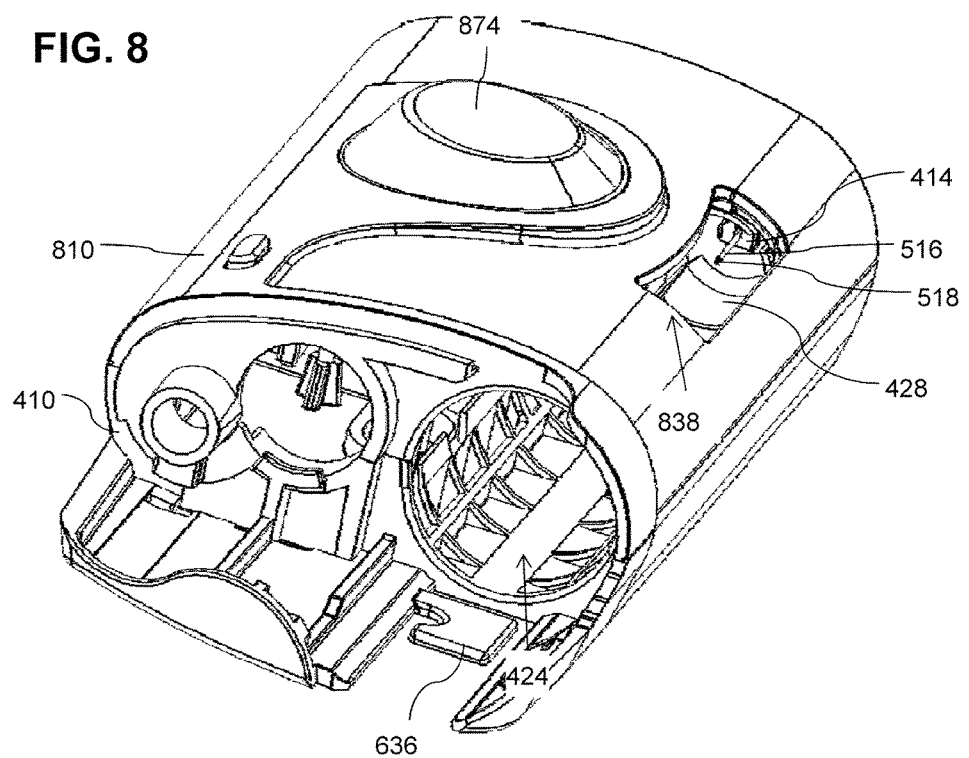
FIG. 8 is a proximal/dorsal perspective view of the exterior of a delivery device including a system for aligning a coupling to a channel of a drug cartridge in accordance with an embodiment of the present invention.

FIG. 8 is a proximal/dorsal perspective view of the exterior of a delivery device including a system for aligning a coupling to an access channel of a drug cartridge in accordance with an embodiment of the present invention. The alignment system is seen through a window 838 in an upper housing section 810 of the injector. An optionally activation button 874 is shown.

Figure 9:
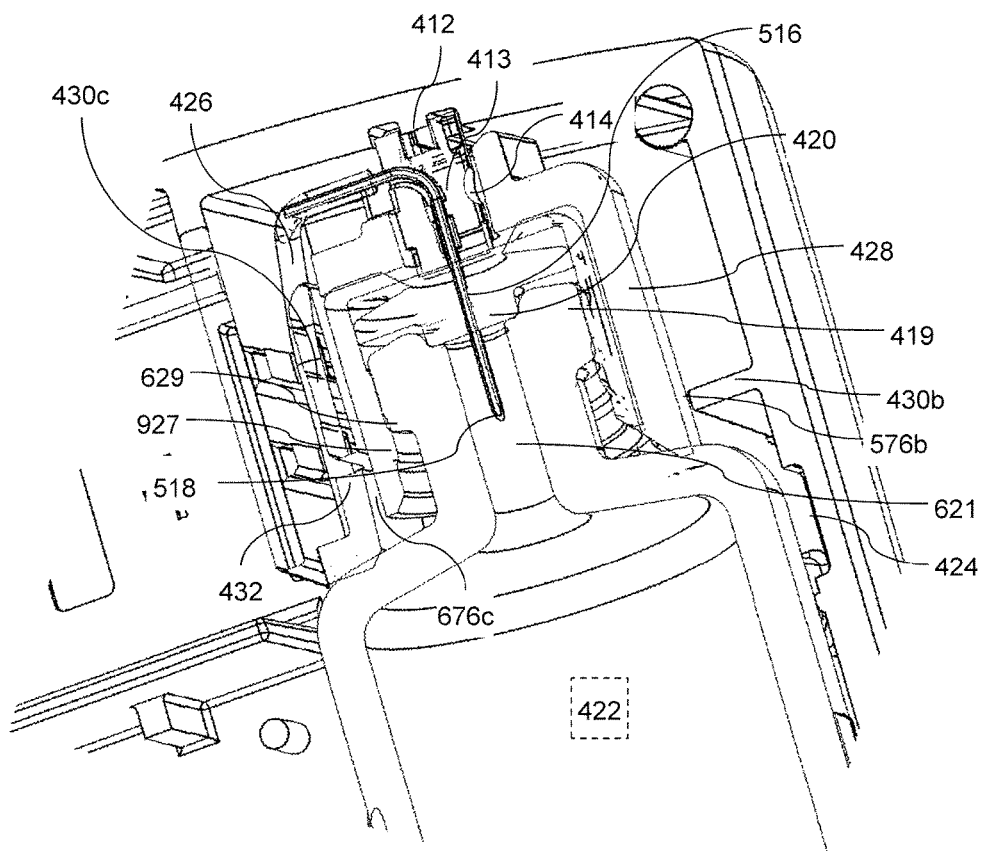
FIG. 9 is a distal perspective view of a system for aligning a coupling to an access channel of a drug cartridge in a loaded position in accordance with an embodiment of the present invention.

FIG. 9 is a distal cross sectional view (cut along a horizontal plane passing through line A-A' of FIG. 5) of a system for aligning a coupling to an access channel of a drug cartridge in a loaded position in accordance with an embodiment of the present invention. Optionally, the in loaded position, cannula 516 has been inserted through septum 420 into channel 621. Optionally cannula 516 forms a fluid path from the inside of cartridge 422 to tube 426.

In some embodiments, in the loaded position, collar 428 is engaged to and/or grasps the distal portion of cartridge 422. For example, collar 428 surrounds the distal portion of cartridge 422 limiting horizontal and/or vertical movement of cartridge 422 with respect to collar 428. Optionally, the distal portion of cartridge 422 butts up against the distal wall of collar 428, limiting distal movement of cartridge 422 with respect to collar 428. Optionally, an interference element 927 locks behind ledge 629, limiting proximal movement of cartridge 422 with respect to collar 428.

Figure 10:
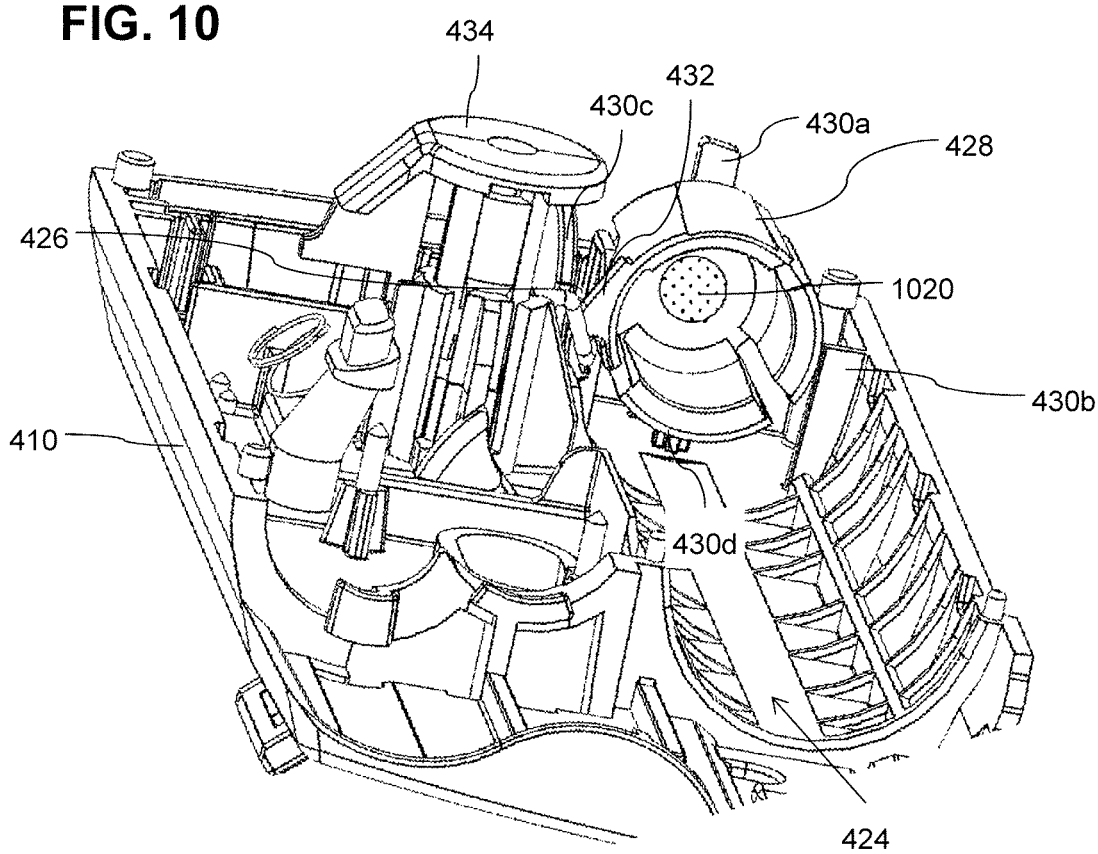
FIG. 10 is a proximal perspective view of an alternative system for aligning a coupling to a channel of a drug cartridge installed in a delivery device in accordance with an embodiment of the present invention.

FIG. 10 is a proximal perspective view of an alternative system for aligning a coupling to an access channel of a drug cartridge installed in a delivery device in accordance with an embodiment of the present invention. For example, in the embodiment of FIG. 10, the coupling of the alignment system includes a septum 1020. Optionally in the exemplary embodiment of FIG. 10 the cartridge includes a cannula for piercing septum 1020.

Figure 11:
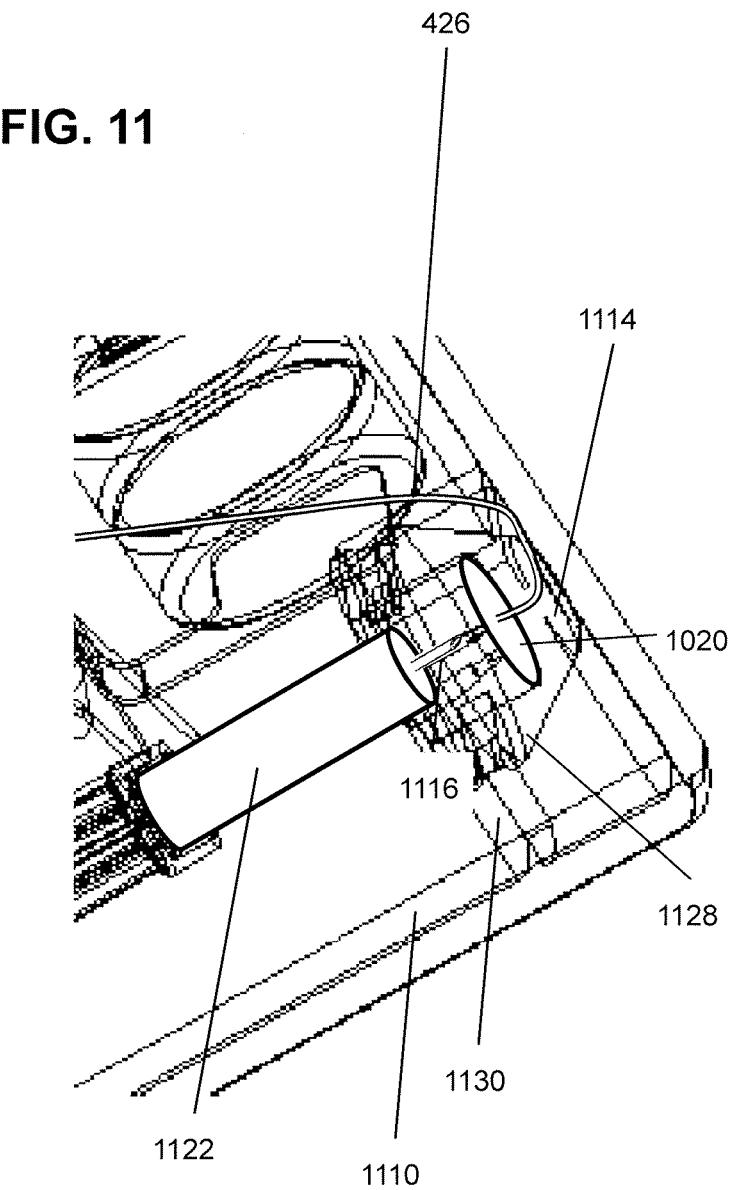
FIG. 11 is a dorsal perspective view of the distal end of a cartridge and an alternative system for aligning a coupling to a channel of the cartridge in accordance with an embodiment of the present invention.

FIG. 11 illustrates a proximal close up perspective view of an alternative embodiment of a alignment system in accordance with an embodiment of the current invention. In the system of FIG. 11, a movable alignment collar 1128 holds a coupler including a septum 1020. Optionally, when a drug cartridge 1122 is inserted into the device, a cannula 1116 of drug cartridge 1122 pierces septum 1020 to form a fluid connection with an internal fluid path including flexible tube 426. Optionally, collar 1128 is held movably to a housing 1110 of the delivery device by a flexible mount 1114 and/or a support 1130.

It is expected that during the life of a patent maturing from this application many relevant delivery systems, cartridges, and/or coupling technologies and/or flexible supports will be developed and the scope of the terms delivery system, cartridge, collar, coupler, support and/or mount are intended to include all such new technologies a priori.

As used herein the term "about" refers to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An assembly for aligning a cartridge interface of a drug delivery device to an access channel of a cartridge, the assembly comprising:
    a collar having an opening sized and shaped for engaging said cartridge on opposing sides of said access channel;
    a cannula mounted to said collar, a tip region of said cannula extending into the access channel when said collar is engaged to said cartridge;
    a frame including a guide fitting to said cartridge to align and position the access channel with respect to said frame; and
    a first support movably connecting the collar to the frame to align said collar with the cartridge when the cartridge is aligned and positioned to said frame by said guide, thereby aligning the cannula with the access channel, the first support allowing lateral translational movement of said collar relative to the frame to accommodate misalignment of said access channel with respect to said frame, thereby preserving alignment of said cannula with the access channel.

2. The assembly of claim 1, wherein said movement of said collar is elastic.

3. The assembly of claim 1, wherein a measure of misalignment of said cartridge is equal to a deviation tolerance of said positioning of said access channel with respect to said frame.

4. The assembly of claim 1, wherein said preserving of said alignment of said cannula with the access channel is to within an alignment tolerance of said cannula to said access channel.

5. The assembly of claim 1, wherein said first support allows transaxial movement of said tip region of said cannula under a stress, said transaxial movement being more than a transaxial movement due to a flexibility of said frame under said stress.

6. The assembly of claim 1, wherein said first support allows transaxial movement of said tip region of said cannula under a stress, said transaxial movement being more than a transaxial movement due to a flexibility of said cannula under said stress.

7. The assembly of claim 1, wherein said first support allows transaxial movement of said tip region of said cannula more than a deviation tolerance of said positioning of said access channel by said guide.

8. The assembly of claim 1, wherein preserving alignment of said cannula with said access channel is to within a deviation tolerance of a positioning of said cannula with respect to said access channel that is less than a transaxial deviation tolerance of said positioning of said access channel with respect to said frame.

9. The assembly of claim 1, wherein the first support permits more movement of said collar with respect to the frame than a deviation tolerance of positioning of said cannula in said access channel.

10. The assembly of claim 1, wherein said guide includes a channel fitting to a body of said cartridge.

11. The assembly of claim 10, wherein said channel includes an open end opposite said collar and wherein said cartridge slides through said open end into said channel until said cartridge engages said collar.

12. The assembly of claim 1, wherein the collar includes an elastically expanding interface for said engaging to the cartridge.

13. The assembly of claim 1, wherein said first support includes at least one member selected from the group consisting of a flexible mount, a pivoting support, and a support with a slack.

14. The assembly of claim 1, further including:
   a base blocking movement of said cannula away from said cartridge in an axial direction.

15. The assembly according to claim 1, wherein the first support further allows pivotal movement of the collar relative to a longitudinal axis of the collar.

* * * * *